(12) United States Patent
Wiedner

(10) Patent No.: US 7,080,415 B2
(45) Date of Patent: Jul. 25, 2006

(54) SAFETY GLASSES

(75) Inventor: Klaus Wiedner, Furth (DE)

(73) Assignee: Uvex Arbeitsschutz GmbH, Furth (DE)

( * ) Notice: Subject to any disclaimer, the term of this patent is extended or adjusted under 35 U.S.C. 154(b) by 199 days.

(21) Appl. No.: 10/479,280

(22) PCT Filed: Apr. 27, 2002

(86) PCT No.: PCT/EP02/04685

§ 371 (c)(1),
(2), (4) Date: Dec. 1, 2003

(87) PCT Pub. No.: WO02/096330

PCT Pub. Date: Dec. 5, 2002

(65) Prior Publication Data

US 2004/0148684 A1  Aug. 5, 2004

(30) Foreign Application Priority Data

May 30, 2001 (DE) ............................ 201 09 028 U

(51) Int. Cl.
*A61F 9/02* (2006.01)
(52) U.S. Cl. ........................................................ 2/435
(58) Field of Classification Search ............ 2/435–437, 2/452
See application file for complete search history.

(56) References Cited

U.S. PATENT DOCUMENTS

| 2,881,444 | A | * | 4/1959 | Fresh et al. ........................ 2/9 |
| 3,012,248 | A | * | 12/1961 | Kleinman ....................... 2/436 |
| 4,069,516 | A | * | 1/1978 | Watkins, Jr. ................... 2/428 |
| 4,171,543 | A |   | 10/1979 | Cressi |
| 4,290,673 | A | * | 9/1981 | Yamamoto .................... 351/62 |
| 5,802,622 | A | * | 9/1998 | Baharad et al. ................ 2/434 |
| 6,098,204 | A |   | 8/2000 | Arnette |

FOREIGN PATENT DOCUMENTS

| DE | 11 93 639 | 5/1965 |
| EP | 0 815 814 | 1/1998 |
| FR | 2 302 718 | 10/1976 |
| FR | 2 684 292 | 6/1993 |
| WO | WO 95/25491 | 9/1995 |
| WO | WO 97/41815 | 11/1997 |

* cited by examiner

Primary Examiner—Katherine M. Moran
(74) Attorney, Agent, or Firm—Browdy and Neimark, PLLC

(57) ABSTRACT

In safety goggles, in particular industrial safety goggles, comprising a curved sight piece and a soft frame between the sight piece and face contact area, it is provided that the frame is designed in the way of a bellows frame, having at least one fold.

7 Claims, 3 Drawing Sheets

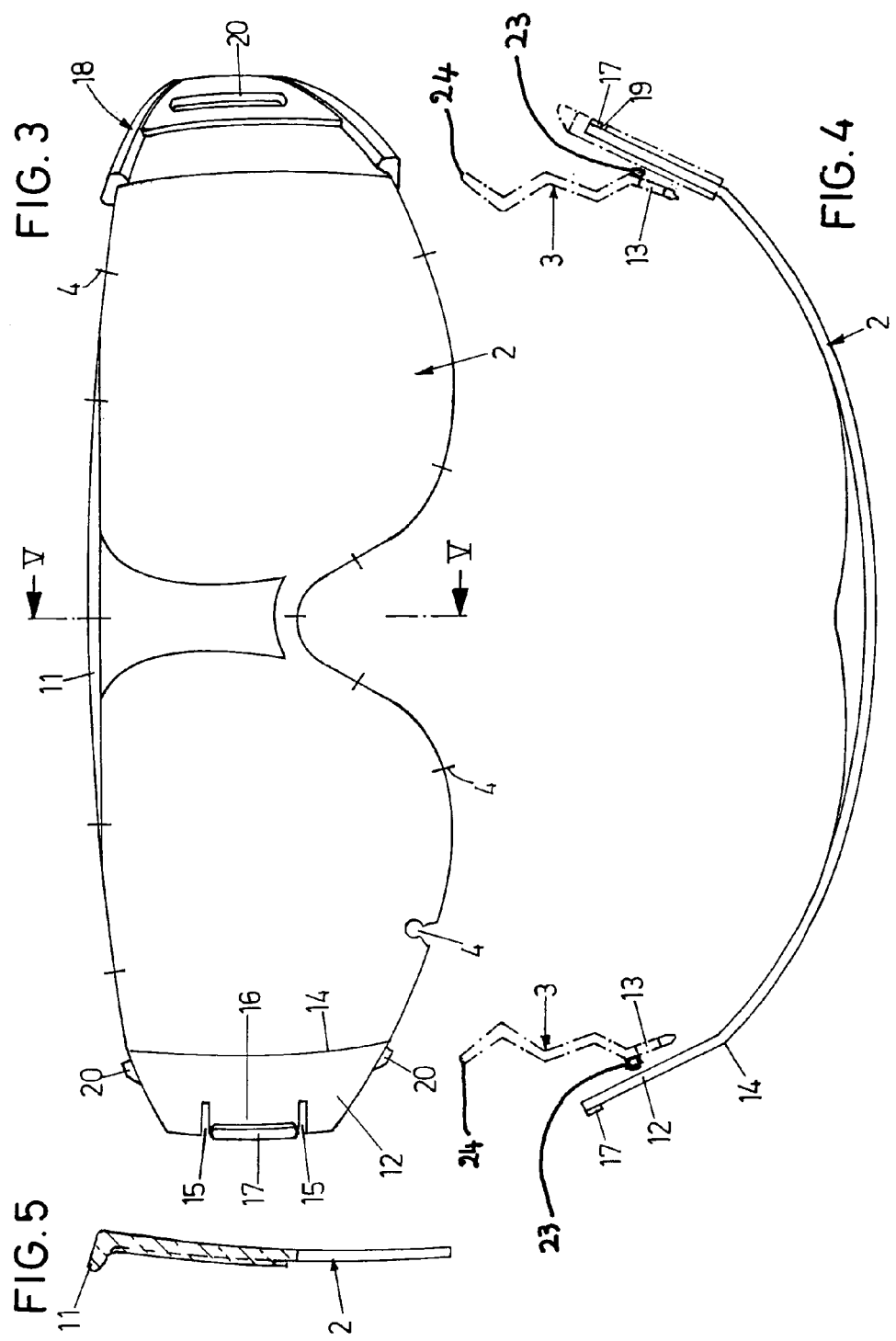

SAFETY GLASSES

BACKGROUND OF THE INVENTION

1. Field of the Invention

The invention relates to safety goggles, in particular industrial safety goggles, comprising a curved sight piece and a soft frame between the sight piece and a face contact area, wherein the frame is designed in the way of a bellows frame, having at lest one fold.

2. Prior Art

Safety goggles of the generic type are known from DE 11 93 639 B1.

OBJECT AND SUMMARY OF THE INVENTION

It is an object of the invention to embody safety goggles that enable the frame and face contact area to be optimally adapted to a user's anatomy, thus ensuring high convenience of wearing and optimal safety.

According to the invention, this object is attained in that the frame encompasses the top of the sight piece, leaving an airing gap.

A fold or several folds of this type, which are known per se, produce great flexibility, creating high convenience of wearing accompanied with a shock absorbing crumple zone that adapts automatically to anatomic requirements, with the fold or folds being preferably designed to encircle the entire sight piece. This provides for total protection to all sides against any penetration of light, particles and splashes.

The airing gap according to the invention ensures that there is no direct passage between the outside and interior of the goggles, but nevertheless excellent airing conditions.

Provision may further be made for the lateral ends of the sight piece to reach over the frame laterally, with airing holes being provided in this area between the sight piece and frame, which will still further improve the airing conditions. The sight piece simultaneously works as a cover for the airing holes.

Preferably, head strap clasps are lockable into place on the lateral ends of the sight piece. This design works to advantage as such as well as in combination with a bellows frame, replacement of the sight piece thus being easily possible and the sight piece itself being able of assuming a kind of load-bearing function. A head strap is fastened to the head strap clasps in a manner known per se.

This design also offers the possibility of ease of handling by automats during manufacture.

By advantage, the approximately vertical lateral edge of the sight piece forms a locking projection for snap-engagement with the head strap clasps, the locking projection cooperating with a corresponding locking recess on the head strap clasp.

In the vicinity of the airing holes between the frame and the lateral ends of the sight piece, provision can be made for spacers which will keep the airing holes free even when the sight piece is pressed against the frame under tension by the head strap.

For greater flexibility, the lateral ends of the sight piece may be slit on both sides of the locking projection.

Additional locking projections may be provided in the vicinity of the top and bottom edge of the sight piece.

BRIEF DESCRIPTION OF THE DRAWINGS

Details of the invention will become apparent from the ensuing description of a preferred embodiment, taken in conjunction with the drawing, in which:

FIG. 3 is an elevation of the sight piece, with a head strap clasp locked in place on the right;

FIG. 4 is a plan view of the sight piece of FIG. 3;

FIG. 5 is a sectional view on the line IV—IV of FIG. 3;

DETAILED DESCRIPTION OF THE PREFERRED EMBODIMENT OF THE INVENTION

Figure 1:
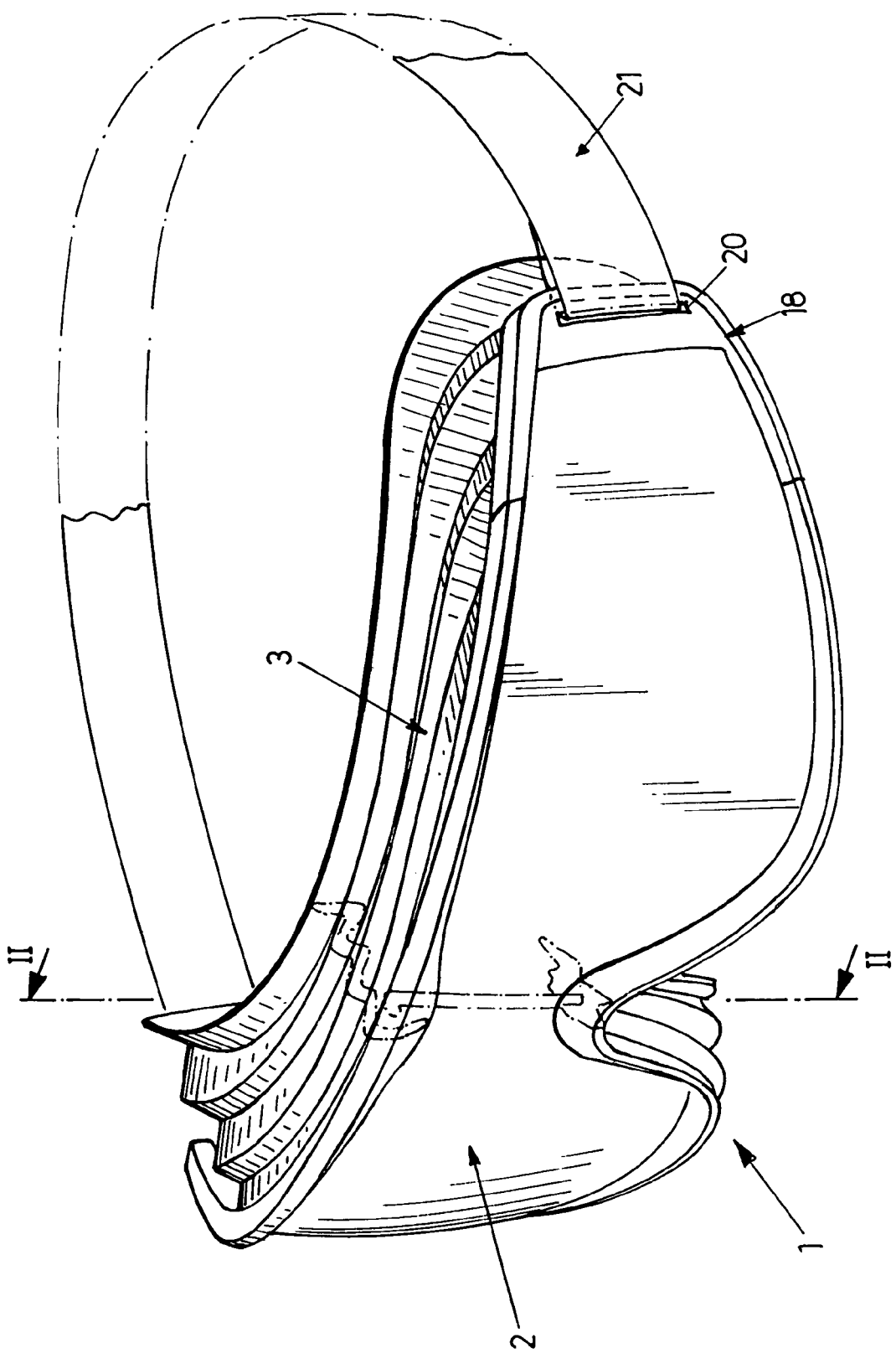
FIG. 1 is a perspective view of a pair of safety goggles according to the invention.

As seen in the drawing, a pair of safety goggles 1 comprises a one-piece continuous, curved sight piece 2 and a soft frame 3.

The rigid, inherently stable sight piece 2 supports the frame 3, which is mounted on the sight piece in a manner known per se by way of keyhole notches 4. Only one of these keyhole notches is plotted in FIG. 3, the rest being roughly outlined by marks.

The frame 3 is joined to the sight piece 2 in the vicinity of the top edge 5 thereof in such a way that an air gap 6 is left free that is covered by the lowered outer edge 7 at the front of the frame 3.

Figure 2:
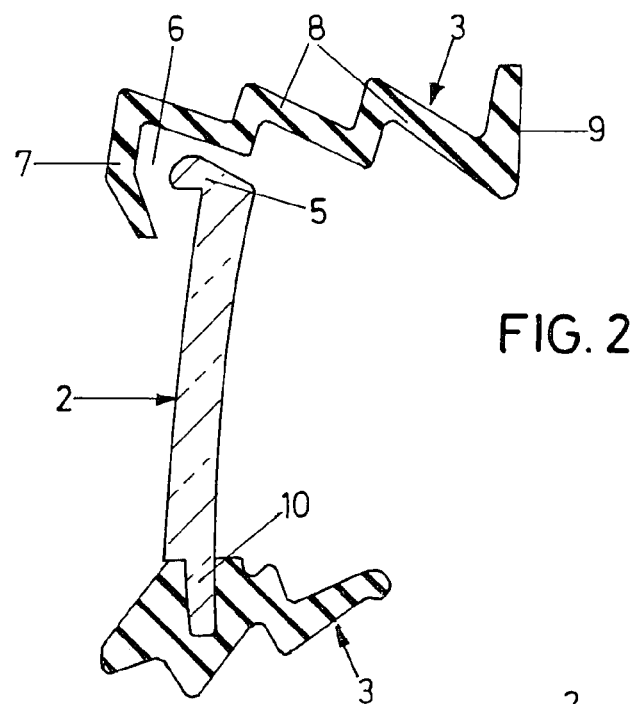
FIG. 2 is a sectional view on the line II—II of FIG. 1.
Figure 6:
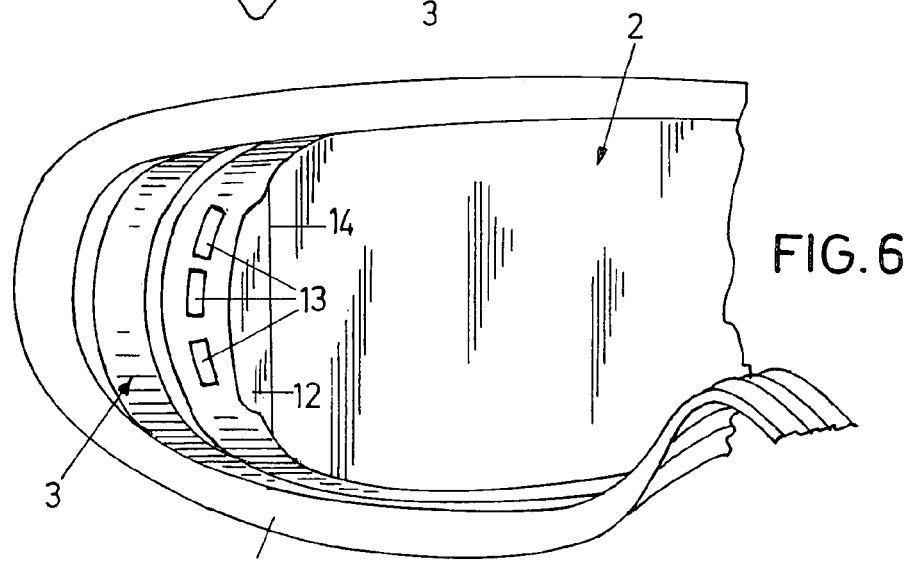
FIG. 6 is a perspective partial view of the pair of safety goggles from inside.
Figure 7:
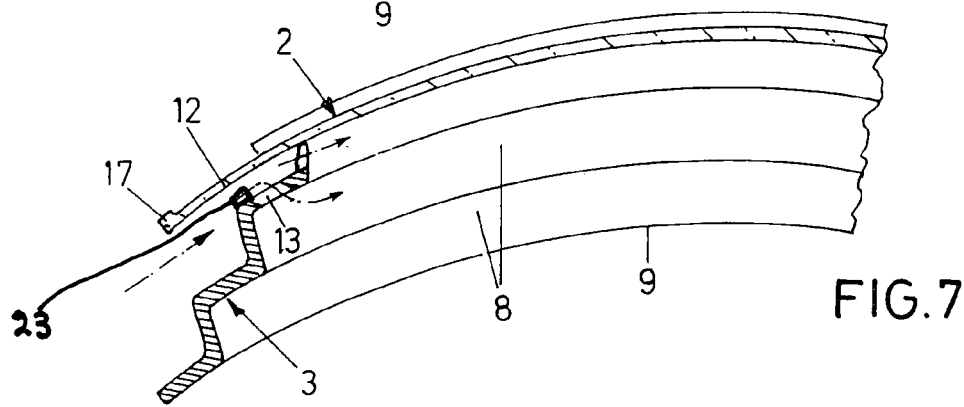
FIG. 7 is a partial plan view of the area, seen in FIG. 6, of the pair of safety goggles.

As seen in particular in FIGS. 1 and 2, the frame 3 forms sort of a bellows frame, correspondingly comprising several folds 8, which helps accomplish great flexibility and adaptability so that the face contact area 9 will always fit a user's face tightly and nonetheless conveniently regardless of the specific anatomic requirements.

In the vicinity of the bottom edge 10 of the sight piece 2, the frame 3 encompasses the sight piece 2, having positive fit.

As seen in FIG. 5, the top of the sight piece 2 has a projection 11 that stands out to the front. This projection 11 serves for holding the frame 3 and simultaneously works as a spacer for the production of space between the top of the sight piece 2 and the frame 3, forming an airing gap. For this effect still to be increased, provision can be made for additional knobbed spacers in the vicinity of the projection 11 and/or for one or several recesses in the sight piece which will however be covered to the front by the frame.

In the vicinity of the lateral ends 12, the frame 3 is provided with airing holes 13 which are covered by the lateral ends 12 that are bent at 14 in discontinuity of the curved sight piece so that neither light nor particles nor splashes are admitted to the inside through the airing holes 13.

In this area, the frame is provided with knobbed spacers 23 shown in FIG. 4 which prevent the lateral airing holes from being shut when tension is exercised on the free ends 24 of the lateral ends 12 of the sight piece by the head strap.

As seen on the left in FIG. 3, two slits 15 at the lateral ends 12 form a flexible tongue 16 that is provided with a locking projection 17 in the vicinity of the vertical outer edge.

Head strap clasps 18 can be locked on to the lateral ends; one of them is shown on the right in FIG. 3. The head strap clasps 18 have a locking recess 19 with which to snap-engage the locking projections 17. Additionally, projections (not shown) may be provided in the vicinity of the top edge and bottom edge of the lateral ends of the sight piece 2, snap-engaging with corresponding recesses of the head strap clasps 18. By advantage, the locking recesses 19 have the shape of a widening (see FIG. 3 on the right) of slots 20. For replacement of the sight piece 2, the locking projections 17 only have to be pushed down from outside so that they disengage from the locking recesses 19.

The head strap clasps 18 are provided with slots 20 through which to pass a head strap 21.

The invention claimed is:

1. A pair of safety goggles (1), in particular industrial safety goggles, comprising a curved sight piece (2) with lateral sight-piece ends (12) and a soft frame (3) between the sight piece and face contact area, wherein the frame is designed in the way of a bellows frame, having at least one fold, characterized in that free ends of the lateral sight-piece ends (12) are respectively spaced apart from free ends (24) of the frame (3), wherein the frame (3) has airing holes (13) which are located on opposite ends of and between a top edge and a bottom edge of the frame behind the sight-piece ends so that the airing holes are covered by the lateral sight-piece ends.

2. A pair of safety goggles according to claim 1, characterized in that the at least one fold is designed to encircle the sight piece (2).

3. A pair of safety goggles according to claim 1, characterized in that the frame (3) encompasses the top of the sight piece, leaving an airing gap.

4. A pair of safety goggles according to claim 1, characterized in that in the vicinity of the airing holes between the frame (3) and lateral sight-piece end (12), spacers are provided between the sight piece (2) and frame (3).

5. A pair of safety goggles according to claim 1, characterized in that head strap clasps (18) are lockable into place on the lateral sight-piece ends (12).

6. A pair of safety goggles according to claim 5, characterized in that the approximately vertical lateral edge of the sight piece is designed as a locking projection (17) for snap-engagement with the head strap clasps (18).

7. A pair of safety goggles according to claim 6, characterized in that the lateral sight-piece ends (12) are slit on either side of the locking projection (17).

* * * * *